United States Patent
Vanrompay

(10) Patent No.: US 10,393,742 B2
(45) Date of Patent: Aug. 27, 2019

(54) **METHOD AND PEPTIDES FOR THE DETECTION OF *CHLAMYDIA SUIS***

(71) Applicant: Universiteit Gent, Ghent (BE)

(72) Inventor: Daisy Vanrompay, Oosterzele (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 15/560,582

(22) PCT Filed: Mar. 22, 2016

(86) PCT No.: PCT/EP2016/056190
§ 371 (c)(1),
(2) Date: Sep. 22, 2017

(87) PCT Pub. No.: WO2016/150930
PCT Pub. Date: Sep. 29, 2016

(65) Prior Publication Data
US 2018/0045726 A1 Feb. 15, 2018

(30) Foreign Application Priority Data
Mar. 24, 2015 (EP) .................................. 15160478

(51) Int. Cl.
| | | |
|---|---|---|
| *A61K 39/00* | (2006.01) |
| *A61K 39/118* | (2006.01) |
| *C12Q 1/00* | (2006.01) |
| *G01N 33/569* | (2006.01) |
| *C07K 7/06* | (2006.01) |
| *C07K 7/08* | (2006.01) |
| *C07K 14/295* | (2006.01) |
| *C07K 17/00* | (2006.01) |

(52) U.S. Cl.
CPC ......... *G01N 33/56927* (2013.01); *C07K 7/06* (2013.01); *C07K 7/08* (2013.01); *C07K 14/295* (2013.01); *C07K 17/00* (2013.01); *G01N 2333/295* (2013.01); *G01N 2469/20* (2013.01)

(58) Field of Classification Search
CPC .............................. A61K 39/00; A61K 39/118
USPC .................... 424/184.1, 185.1, 234.1, 263.1
See application file for complete search history.

(56) References Cited

FOREIGN PATENT DOCUMENTS

WO 2014/146663 9/2014

OTHER PUBLICATIONS

International Search Report dated May 17, 2016 in International (PCT) Application No. PCT/EP2016/056190.
Written Opinion of the International Searching Authority dated May 17, 2016 in International (PCT) Application No. PCT/EP2016/056190.
Extended European Search Report dated Sep. 21, 2015 in corresponding European Patent Application 15160478.2.
Eggemann, G., M. Wendt, et al. (2000). "Prevalence of Chlamydial infections in breeding sows and their correlation to reproductive failure." DTW. Deutsche tierarztliche Wochenschrift 107(1): 3-10.
Evelien De Clercq et al.: (2014). "The Immune 1-15 Response Against Chlamydia Suis Genital Tract Infection Partially Protects Against Re-Infection", Veterinary Research, Biomed Central Ltd, London, UK, vol. 45, No. 1, 25, p. 95.
Borel, N., N. Regenscheit, et al. (2012). "Selection for Tetracycline-Resistant Chlamydia Suis in Treated Pigs." Vet Microbiol 156(1-2): 143-146.
Brade, L., Rozalski, A., Kosma, P., Brade, H. (2000). "A Monoclonal Antibody Recognizing the 3-deoxy-D-manno-oct-2-ulosonic acid (Kdo) trisaccharide αKdo(2→4)αKdo(2→4)αKdo of Chlamydophila psittaci 6BC lipopolysaccharide." Journal of Endotoxin Research 6(5): 361-368.
De Puysseleyr, K., L. De Puysseleyr, et al. (2014). "Evaluation of the presence and zoonotic transmission of Chlamydia suis in a pig slaughterhouse." BMC Infectious Diseases 14: 560 (1-6).
De Puysseleyr, K., L. De Puysseleyr, et al. (2014). "Development and Validation of a Real-Time PCR for Chlamydia suis Diagnosis in Swine and Humans," PloS one 9(5): e96704 (1-7).
Di Francesco, A., R. Baldelli, et al. (2006). "Seroprevalence to chlamydiae in pigs in Italy." Veterinary Record 159(25): 849-850.
Donati, M., A. Di Francesco, et al. (2009). "In vitro detection of neutralising antibodies to Chlamydia suis in pig sera." Veterinary Record 164(6): 173-174.
Forsbach-Birk, V., C. Foddis, et al. (2013). "Profiling Antibody Responses to Infections by Chlamydia abortus Enables Identification of Potential Virulence Factors and Candidates for Serodiagnosis." PloS one 8(11): e80310 (1-15).
Grimwood, J. and R. S. Stephens (1999). "Computational analysis of the polymorphic membrane protein superfamily of Chlamydia trachomatis and Chlamydia pneumoniae." Microbial & Comparative Genomics 4(3): 187-201.
Hoelzle, L. E., K. Hoelzle, et al. (2004). "Recombinant major outer membrane protein (MOMP) of Chlamydophila abortus, Chlamydophila pecorum, and Chlamydia suis as antigens to distinguish chlamydial species-specific antibodies in animal sera." Veterinary Microbiology 103(1-2): 85-90.
Hoelzle, L. E., G. Steinhausen, et al. (2000). "PCR-based detection of chlamydial infection in swine and subsequent PCR-coupled genotyping of chlamydial omp1-gene amplicons by DNA-hybridization, RFLP-analysis, and nucleotide sequence analysis." Epidemiology and Infection 125(2): 427-439.
Ivanov, V. S., Z. K. Suvorova, et al. (1992). "Effective Method for Synthetic Peptide Immobilization That Increases the Sensitivity and Specificity of ELISA Procedures." Journal of Immunological Methods 153(1-2): 229-233.
Lis, P., A. Kumala, et al. (2014). "Novel locked nucleic acid (LNA)-based probe for the rapid identification of Chlamydia suis using real-time PCR." BMC Veterinary Research 10: 225 (1-6).

(Continued)

*Primary Examiner* — Rodney P Swartz
(74) *Attorney, Agent, or Firm* — Wenderoth, Lind & Ponack, L.L.P.

(57) ABSTRACT

The present invention relates to a method for detecting and diagnosing *Chlamydia suis* infections in a subject, and a diagnostic kit therefor.

15 Claims, No Drawings
Specification includes a Sequence Listing.

(56) References Cited

OTHER PUBLICATIONS

Longbottom, D., S. Fairley, et al. (2002). "Serological diagnosis of ovine enzootic abortion by enzyme-linked immunosorbent assay with a recombinant protein fragment of the polymorphic outer membrane protein POMP90 of Chlamydophila abortus." Journal of Clinical Microbiology 40(11): 4235-4243.

Longbottom, D., E. Psarrou, et al. (2001). "Diagnosis of ovine enzootic abortion using an indirect ELISA (rOMP91B iELISA) based on a recombinant protein fragment of the polymorphic outer membrane protein POMP91B of Chlamydophila abortus." FEMS Microbiology Letters 195(2): 157-161.

Marques, P. X., P. Souda, et al. (2010). "Identification of immunologically relevant proteins of Chlamydophila abortus using sera from experimentally infected pregnant ewes." Clinical and Vaccine Immunology 17(8): 1274-1281.

Niessner, A., C. Kaun, et al. (2003). "Polymorphic membrane protein (PMP) 20 and PMP 21 of Chlamydia pneumoniae induce proinflammatory mediators in human endothelial cells in vitro by activation of the nuclear Factor-κB pathway." The Journal of Infectious Diseases 188(1): 108-113.

Sachse, K., E. Vretou, et al. (2009). "Recent developments in the laboratory diagnosis of chlamydial infections." Veterinary Microbiology 135(1-2): 2-21.

Schautteet, K., D. S. A. Beeckman, et al. (2010). "Possible pathogenic interplay between Chlamydia suis, Chlamydophila abortus and PCV-2 on a pig production farm" Veterinary Record 166(11): 329-333.

Schautteet, K., E. De Clercq, et al. (2013). "Tetracycline-resistant Chlamydia suis in cases of reproductive failure on Belgian, Cypriote and Israeli pig production farms." Journal of Medical Microbiology 62: 331-334.

Schautteet, K., E. Stuyven, et al. (2011). "Protection of pigs against Chlamydia trachomatis challenge by administration of a MOMP-based DNA vaccine in the vaginal mucosa." Vaccine 29(7): 1399-1407.

Schautteet, K. and D. Vanrompay (2011). "Chlamydiaceae infections in pig." Veterinary Research 42(1): 29 (1-10).

Stephens, R. S., S. Kalman, et al. (1998). "Genome sequence of an obligate intracellular pathogen of humans: Chlamydia trachomatis." Science 282(5389): 754-759.

Szeredi, L., I. Schiller, et al. (1996). "Intestinal Chlamydia in finishing pigs." Veterinary Pathology 33(4): 369-374.

Tan, C., R. C. Hsia, et al. (2009). "Chlamydia trachomatis-Infected Patients Display Variable Antibody Profiles against the Nine-Member Polymorphic Membrane Protein Family." Infection and Immunity 77(8): 3218-3226.

Vanrompay, D., T. Geens, et al. (2004). "Immunoblotting, ELISA and culture evidence for Chlamydiaceae in sows on 258 Belgian farms." Veterinary Microbiology 99(1): 59-66.

Verminnen, K., M. Van Loock, et al. (2006). "Evaluation of a recombinant enzyme-linked immunosorbent assay for detecting Chlamydophila psittaci antibodies in turkey sera." Veterinary Research 37(4): 623-632.

Wang, J., L. L. Chen, et al. (2009). "A chlamydial type III-secreted effector protein (Tarp) is predominantly recognized by antibodies from humans infected with Chlamydia trachomatis and induces protective immunity against upper genital tract pathologies in mice." Vaccine 27(22): 2967-2980.

Wang, J., Y. Q. Zhang, et al. (2010). "Immunodominant Regions of a Chlamydia trachomatis Type III Secretion Effector Protein, Tarp." Clinical and Vaccine Immunology 17(9): 1371-1376.

Wehrl, W., V. Brinkmann, et al. (2004). "From the inside out—processing of the Chlamydial autotransporter PmpD and its role in bacterial adhesion and activation of human host cells." Molecular Microbiology 51(2): 319-334.

Wittenbrink, M. M., X. T. Wen, et al. (1991). "Bacteriological Investigations into the Incidence of Chlamydia-Psittaci in Organs from Swine and in Aborted Porcine Fetuses." Journal of Veterinary Medicine Series B-Zentralblatt Fur Veterinarmedizin Reihe B-Infectious Diseases and Veterinary Public Health 38(6): 411-420 (English Summary).

Zahn, I., L. Szeredi, et al. (1995). "Immunohistological Determination of Chlamydia psittaci/Chlamydia pecorum and C. trachomatis in the Piglet Gut" Journal of Veterinary Medicine Series B-Zentralblatt Fur Veterinarmedizin Reihe B-Infectious Diseases and Veterinary Public Health 42(5): 266-276 (English Summary).

Cevenini, R., M. Donati, et al. (1991). "Partial Characterization of an 89-kDa Highly Immunoreactive Protein from Chlamydia-Psittaci A/22 Causing Ovine Abortion." FEMS Microbiology Letters 81(1): 111-116.

METHOD AND PEPTIDES FOR THE DETECTION OF *CHLAMYDIA SUIS*

FIELD OF THE INVENTION

The present invention relates to a method for detecting and diagnosing *Chlamydia suis* infections in a subject, and a diagnostic kit therefor.

BACKGROUND OF THE INVENTION

Chlamydiaceae species are well known pathogens, and cause a wide variety of symptoms in both animals and humans (Longbottom and Coulter 2003). Beside the well documented zoonotic potential of *Chlamydia* (C). *abortus* and *C. psittaci*, only recently, a few studies report the isolation of *C. suis* strains from human eyes (Dean et al. 2013; De Puysseleyr et al. 2014). The source of a zoonotic *C. suis* infection is the pig, the only animal host for this bacteria. Although *C. suis* is considered to be the most prevalent chlamydial species, pigs can also become infected by *C. pecorum*, *C. abortus* and *C. psittaci* (Schautteet and Vanrompay 2011). Porcine chlamydial infections are not always associated with symptoms, but if so, they lead to important economic losses due to arthritis, pericarditis, polyserositis, pneumonia, conjunctivitis, enteritis, diarrhea and reproductive failure (Zahn et al. 1995; Andersen and Rogers 1998; Eggemann et al. 2000). Diagnosed infections are commonly treated with tetracycline antibiotics, however, more and more tetracycline resistant *C. suis* strains are emerging (Andersen and Rogers 1998; Schautteet et al. 2010; Di Francesco et al. 2011; Borel et al. 2012; Schautteet et al. 2013). In vitro transfer of the antibiotic resistance genes between chlamydial species is demonstrated by Suchland et al. (Suchland et al. 2009). These findings raise another point of concern associated with the possible zoonotic character of *C. suis*. Co-infection of a human individual with a tetracycline resistant ($Tc^R$) *C. suis* and the phylogenetically closely related human pathogen *C. trachomatis*, creates the ideal setting for transfer of the resistance gene and emergence of a $Tc^R$ *C. trachomatis* strain. To avoid creation of multi-resistant strains, comprehensive knowledge about the epidemiology and infection biology of *C. suis* is required. Recent efforts were done to develop *C. suis* specific molecular tests (De Puysseleyr et al. 2014; Lis et al. 2014) and to apply these analyses to investigate the presence of *C. suis* in a human risk population (De Puysseleyr et al. 2014). However, detection of viable *C. suis* bacteria in animal or human samples provides no information about the presence of an existent infection of this microbe. Serological tests to detect the presence of anti-*C. suis* antibodies are able to actually prove the presence of an immunological response and thus an infection. Unfortunately, at present, no assay for *C. suis* specific serodiagnosis is available.

Numerous serological assays targeting chlamydial antigens or anti-chlamydial antibodies are published (Sachse et al. 2009). Assays based on detection of antibodies directed against the surface exposed lipopolysaccharide (LPS) (Wittenbrink et al. 1991) or the synthetic neoglycoconjugate containing the trisaccharide alphaKdo(2→4)alphaKdo (2→4)alphaKdo (Kdo, 3-deoxy-D-manno-oct-2-ulopyranosonic acid) which represents a structure of the lipopolysaccharide (LPS) (Brade et al., 2000) and against the full length proteins or peptides from the major outer membrane protein (MOMP) (Vanrompay et al. 2004; Medac, Wedel, Germany), polymorphic outer membrane proteins (Pmps) (Longbottom et al. 2001; Longbottom et al. 2002) or whole elementary body (EB) preparations (Di Francesco et al. 2006), were developed with varying degrees of success in terms of sensitivity and specificity. However, in some cases, cross-reactivity between *Chlamydia* species can hinder interpretation of results (Donati et al. 2009). Hoelzle et al. demonstrated the suitability of the full length recombinant MOMP proteins of *C. suis*, *C. abortus* and *C. pecorum* in ELISA assays to identify the infecting chlamydial species (Hoelzle et al. 2004). However, until now, this approach has not been further verified in animals in the field. Furthermore, a recombinant protein fragment of the Pmp90 was successfully used for serological diagnosis of *C. abortus* infections (Longbottom et al. 2001). The Pmps are considered as important virulence factors and several studies demonstrated the induction of an immune response (Grimwood and Stephens 1999; Niessner et al. 2003; Wehrl et al. 2004) and even protective immunity (Cevenini et al. 1991). Tan et al. (2009) demonstrated that the Pmps elicit various serologic responses in *C. trachomatis*-infected patients. However, differences in the strengths and specificities of the Pmp subtype-specific antibody reactivity related to gender and clinical outcome were observed. This indicates that the Pmp gene family forms the basis of a mechanism of antigenic variation. The PmpD protein of *C. abortus* was recognized as a major antigen using sera of experimentally infected ewes. In addition, also the MOMP protein and the translocated actin recruitment protein (Tarp) were identified as reactive proteins in this study (Marques et al. 2010; Forsbach-Birk et al. 2013). The Tarp protein is also predominantly recognized by antibodies from humans infected with *C. trachomatis* (Wang et al. 2009).

Specific detection of anti-*C. suis* antibodies can provide the evidence for an existent infection in pigs and humans, an essential factor in the study of the zoonotic transfer of this microbe. Unfortunately, to date, no sensitive *C. suis* specific assay is available for animal or human serodiagnosis and no studies to identify the major reactive antigens of *C. suis* have been published until today. In fact, seroprevalence studies in pigs are based on detection of antibodies against LPS, MOMP and whole EB preparations and serological cross-reactions with antibodies against other chlamydial species or other pathogens do occur (Schautteet and Vanrompay 2011).

There is thus currently still a need for antigenic peptides that are useful in the detection or diagnosis of *Chlamydia suis* in a subject.

SUMMARY OF THE INVENTION

The present invention encompasses a *C. suis* specific and antigenic peptide, in particular for serodiagnostic use, and a kit comprising said peptide.

Thus, one embodiment of the present invention relates to a peptide comprising or consisting essentially of the amino acid sequence as represented by SEQ ID NO: 1 or SEQ ID NO: 2, or a variant thereof. In a specific embodiment, the peptide is about and between 7 to 30 amino acids long.

In a further embodiment, the invention relates to a method for diagnosing a *Chlamydia suis* infection in a subject. In particular, the invention comprises a method for detecting the presence of *Chlamydia suis* in a subject, comprising
providing a biological sample from a subject, and
analyzing the sample for the presence of antibodies against a peptide of about 7 to 30 amino acids long, said peptide comprising an amino acid sequence substantially identical to the sequence represented by SEQ ID NO: 1, and/or against a peptide of about 7 to 30 amino acids long, said peptide comprising an amino acid sequence substantially identical to the sequence represented by SEQ ID NO: 2,
whereby the presence of antibodies against one or both peptides is indicative for the presence of *Chlamydia suis* in the subject.

In some embodiments of this aspect of the invention the method comprises one or all of the following steps:
a surface is provided, where the peptide(s) as disclosed herein are attached;
blood or other (fluid) sample obtained from a subject is contacted, optionally after removal of irrelevant components, with the surface under conditions allowing for the specific binding of an antibody to an epitope;
detecting the antibody-peptide complex and/or determining the amount of the bound antibody;
optionally, a washing step is inserted between the first and the second step to remove any sample components that did not interact with the surface. Another washing step may follow the second contacting step and precede the determination.

Preferably, the biological sample is from a mammal, in particular a human or a pig.

In a particular embodiment, the detection of antibodies is conducted using an immunoassay, such as an ELISA. Typically, the biological sample to be tested is a smear or body fluid, preferably mucosal secretions or blood, in particular serum.

Diagnosis is possible at an early stage of the disease, during therapy, as well as after clearance of the infection. In addition, the peptides can be useful to differentiate a vaccinated from an infected subject (DIVA principle). Another embodiment of the present invention relates to *Chlamydia suis* antigenic peptides and a kit comprising these peptides, in particular for the use in a method according to the present invention, namely for detecting the presence of *C. suis* in a subject. Preferably, the test kit is an ELISA.

The invention also relates to the use of the peptide(s) or kit in the diagnosis of *C. suis* infection in a subject, and to a method of preparing said peptide(s) or kit.

DESCRIPTION OF THE INVENTION

As used herein, the singular forms "a", "an", and "the" include both singular and plural referents unless the context clearly dictates otherwise. The terms "comprising", "comprises" and "comprised of" as used herein are synonymous with "including", "includes" or "containing", "contains", and are inclusive or open-ended and do not exclude additional, non-recited members, elements or method steps. The term "about" as used herein when referring to a measurable value such as a parameter, an amount, a temporal duration, and the like, is meant to encompass variations of +/−20% or less, preferably +1-10% or less, more preferably +/−5% or less, of and from the specified value, insofar such variations are appropriate to perform in the disclosed invention. It is to be understood that the value to which the modifier "about" refers is itself also specifically, and preferably, disclosed. Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any >3, >4, >5, >6 or >7 etc. of said members, and up to all said members. All references, and teachings specifically referred to, cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Reference throughout this specification to "one embodiment" or "an embodiment" means that a particular feature, structure or characteristic described in connection with the embodiment is included in at least one embodiment of the present invention.

The present invention relates to peptides, a kit and a method for diagnosing or detecting *Chlamydia* suis infection in a subject. The method is based on the detection of antibodies specifically recognizing immunoreactive peptides derived from the major outer membrane protein (MOMP) and/or polymorphic membrane protein C (PmpC) of *Chlamydia suis*.

The detection of antibodies in animal chlamydial infections has multiple purposes, i.e. confirmation of clinical disease or confirmation of the presence or absence of infection, performance of epidemiological surveys to estimate the prevalence of infection, or the determination of immune status after vaccination.

Since *C. suis* and *C. trachomatis* are phylogenetically closely related and the availability of *C. suis* sequence information is rather limited, the selection of a specific antigen is rather complex. Therefore, the present invention focused on the identification of eight-amino acid peptide antigens to minimize cross-reactions to other pathogens. The in silico analysis of the *C. suis* translocated actin-recruiting phosphoprotein (Tarp) and polymorphic membrane protein (Pmp) was based on the sequences of two strains, and the in vitro screening was executed with sera of 3 other strains. The methodology screens for peptides that are representative antigens for all used *C. suis* strains and led to the selection of three peptides (one Tarp, one PmpC and one MOMP) for further testing using experimentally generated positive and negative control sera. It was for the first time demonstrated in the present invention that the identified MOMP and PmpC peptide antigens are particularly useful in the serodiagnosis of *C. suis*, particularly in swine.

The present invention thus relates to epitopes derived from the MOMP and PmpC of *C. suis* which are specifically recognized by antibodies. In particular, said epitopes consist of an amino acid sequence identical or substantially identical to the sequence represented by SEQ ID NO: 1 (GTK-DASID) or SEQ ID NO: 2 (SQQSSIAS).

In a further embodiment, the invention relates to a peptide, in particular an immune reactive peptide, comprising the epitopes of the present invention. As used herein "immune reactive peptides" or "peptide antigens" refers to (poly)peptides of at least about 7 amino acid residues, like 6, 7, or 8, and up to 35 or 40 amino acid residues long. Said peptides are typically about 7 to 30 amino acids long, in particular about 8 to 25 amino acids, more in particular about 8 to 20, and even more particular about 8 to 15 amino acids long, including all integers in between. The immune reactive peptides as disclosed herein may be used singly or in combination. In a preferred embodiment, the current invention encompasses a peptide consisting of the amino acid sequence disclosed in SEQ ID NOs: 1 or 2, and the use thereof. The peptides of the invention may be used alone or, preferably, in combination.

It will be recognized by the skilled person that, within the amino acid sequence defined herein, substitution and/or deletion of one or possibly more of the amino acids can be made without excessive decrease in the reactivity and/or specificity. Such variants, which are functionally equivalent to the present peptides or epitopes but contain certain amino acid residues which may be non-naturally occurring, modified and/or synthetic, are within the scope of the present invention, if they are recognized by antibodies specific to *C. suis*. The skilled person would be aware that the antibody binding ability of epitope analogues containing, for example, single amino acid substitutions, may be determined using a suitable scanning technique. In one embodiment, the peptides may be modified for the purposes of ease of conjugation to a carrier. For example, it may be desirable for some chemical conjugation methods to include a terminal cysteine.

A "substantially identical" sequence (optionally referred to as "variant") is an amino acid sequence that differs from a reference sequence only by one or more conservative substitutions, as discussed herein, or by one or more non-conservative substitutions, deletions, or insertions located at positions of the sequence that do not destroy the biological function of the amino acid molecule. Such a sequence can be any integer from 75% to 99%, or more generally at least 75%, 80%, 85%, 86%, 87%, 88%, 89%, 90%, or 95%, or as much as 96%, 97%, 98%, or 99% identical at the amino acid or nucleotide level to the sequence used for comparison using, for example, FASTA. For polypeptides, the length of comparison sequences may be at least 5, 10, or 15 amino acids, and up to 20, 25, 30 or 40 amino acids (including all integers in between). Sequence identity can be readily measured using publicly available sequence analysis software (e.g. BLAST software available from the National Library of Medicine).

Alternatively, variants may be identified by modifying one of the above peptide sequences and evaluating the antigenic properties, secondary structure and/or hydropathic nature of the modified peptide using, for example, the representative procedures described herein. A "conservative substitution" is one in which an amino acid is substituted for another amino acid that has similar properties, such that one skilled person in the art would expect the nature of the peptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. In a specific embodiment, a substantially identical sequence is derived from a *Chlamydia suis* strain or isolate.

Determining the presence of antibodies against the MOMP and/or pmpC derived peptides or epitopes of the present invention is indicative of *C. suis* infection. More specific, the presence of said antibodies in a subject can be indicative for a past (whereby the infection is cleared), an early or late infection. In addition, detection of antibodies against the peptide(s) of the present invention can be useful in the serological differentiation between vaccine-induced antibodies and antibodies against the field strain ("DIVA" stands for Differentiating Infected from Vaccinated Animals), if the vaccine antigens specifically differ from the peptides of the present invention. Such a marker assay can detect antibodies against those proteins or peptides that are absent in the vaccine. As such, naturally infected animals can be detected in a vaccinated population.

In a specific embodiment, the present invention relates to a method for detecting a *C. suis* infection, said method comprising the steps of:

a) contacting a biological sample with at least one peptide of the invention, optionally coated on a solid phase, for a time and under conditions sufficient for the formation of an antibody/peptide complex, and b) detecting said antibody/peptide complex, the presence of said complex indicating the presence of a *Chlamydia suis* antibody in said biological sample, wherein the presence of an antibody is indicative of a *C. suis* infection.

In one embodiment of the present invention, the method is an in vitro method. In a specific embodiment, the antibodies to be detected are of the IgA, IgM and/or IgG type. As such, qualitative and quantitative detection of antibodies in the biological sample directed against *Chlamydia suis* is possible and recommended to support in diagnosis and/or differentiation of past (IgM/IgG), acute, recent (IgM) and/or chronic infections (IgG).

In particular, it is demonstrated herein that determining the presence of antibodies against the peptides of the invention allows a specific diagnosis of *C. suis* infection. Until today, no diagnostic test for *C. suis* infection is available.

The term "subject" refers to humans or other mammals, in particular pigs or swine, including sows, boars and piglets.

The term "biological sample" as used herein refers to a sample that may be extracted, untreated, treated, isolated, and concentrated from a subject. Suitably, the biological sample is selected from any part of the subject's body, but it is particularly preferred that the biological sample is a body fluid, preferably blood or mucosal secretions such as a mucosal swab or mucosal lavage. The mucosal surfaces of the body are thin and permeable barriers to the interior of the body because of their physiological activities in gas exchange (the lungs), food absorption (the gut), sensory activities (eyes, nose, mouth, and throat), and reproduction (uterus and vagina). In particular, the biological sample is serum of the subject to be diagnosed.

The term "diagnosing" as used herein refers to methods by which a skilled person can estimate and even determine whether or not a subject has suffered or is suffering from a given disease, disorder or condition. The skilled person makes the diagnosis on the basis of one or more diagnostic indicators, namely antibodies, the amount (including presence or absence) of which is indicator for the presence, severity, or absence of the condition. In addition, the peptides of the present invention are particular useful for developing a reliable assay that can differentiate infected from vaccinated subjects (DIVA assay) in case the vaccine antigens (substantially) differ from the peptides disclosed herein.

The term "determining" or "analyzing" as used herein refers to assessing the presence, absence, quantity, level or amount of the respective antibodies within the subject derived sample, including qualitative or quantitative concentration levels of said substances.

In some embodiments of the method as disclosed herein, detecting, determining or analyzing the presence of the antibodies in the sample can include binding of antibodies to the peptide antigen or epitope as disclosed herein, and then detecting either the binding event or the presence of the antibody isolated from the biological sample. Any known method may be used for the detection of peptide binding antibodies in a sample such as body fluids. Methods considered are, by way of non-limiting example, chromatography, mass spectrometry (and combinations thereof), enzymatic assays, electrophoresis and antibody-based assays, such as but not limited to EIA (Enzyme Immuno Assay), RIA (Radio Immuno Assay), Immunoblotting, ELISA (Enzyme Linked ImmunoSorbent Assay), CLIA (ChemiLuminescent Immuno Assay), CEDIA (Cloned Enzyme Donor Immunoassay), CMIA (Chemiluminescent Microparticle Immunoassay), MEIA (Microparticle Enzyme Immunoassay), FPIA (Fluorescence Polarization Immunoassay), GLORIA (Gold-Labeled, Optically read, Rapid Immunoassay), microarray analysis, fully-automated or robotic immunoassays and latex agglutination assays.

Contacting the biological sample with the peptide under conditions effective and for a period of time sufficient to allow the formation of immune complexes, is generally a matter of adding the composition to the sample and incubating the mixture for a period of time long enough for the antibodies to form immune complexes with the peptide presented. Said peptide antibody mixture can be detected by known means and methods. That is, detection of immune complex formation of peptide antibody can be achieved through the application of numerous approaches. These methods are generally based upon the detection of a label or marker, such as any radioactive, fluorescent, biological or enzymatic tags or labels of standard use in the art. Of course, one may find additional advantages through the use of a secondary binding ligand such as a second antibody or a biotine/avidine (streptavidine) ligand binding arrangement as it is known in the art.

As a typical example, the detection method comprises one or more of the following steps. In a first step, the biological sample is contacted and incubated with a immobilized capture (or coat) reagent, i.e. the peptide(s) of the invention. Immobilization conventionally is accomplished by insolubilizing the capture reagent either before the assay procedure, as by adsorption to a water-insoluble matrix or surface or non-covalent or covalent coupling (for example, using glutaraldehyde or carbodiimide cross-linking, with or without prior activation of the support with, e.g., nitric acid and a reducing agent, or afterward, e.g., by immunoprecipitation).

The solid phase used for immobilization may be any inert support or carrier that is essentially water insoluble and useful in immunometric assays, including supports in the form of, e.g. surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like including 96-or 384-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates are suitably employed for capture reagent immobilization. In one embodiment the immobilized peptide(s) is coated on a microtiter plate, and in particular the preferred solid phase used is a multi-well microtiter plate that can be used to analyze several samples at one time, e.g. a microtest 96- or 384-well ELISA plate.

The solid phase is coated with the capture reagent as defined above, which may be linked by a non-covalent or covalent interaction or physical linkage as desired. In a specific embodiment, the peptides contain an N-terminal acetyl group and are C-terminal attached to polyethylene pins via incorporation of an extra cysteine. If covalent, the plate or other solid phase is incubated with a cross-linking agent together with the capture reagent under conditions well known in the art, e.g. such as for 1 hour at room temperature. Commonly used cross-linking agents for attaching the capture reagent to the solid phase substrate include, e.g. 1,1-bis(diazoacetyl)-2-phenylethane, glutaraldehyde, N-hydroxy-succinimide esters, homobifunctional imidoesters, and bifunctional maleimides. Derivatizing agents such as methyl-3-[(p-azidophenyl)-dithio]pro-pi-oimi-date yield photoactivatable intermediates capable of forming cross-links in the presence of light.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, preferably about 1 to 3 hours, or overnight. After coating and blocking, the biological sample to be analyzed, appropriately diluted, is added to the immobilized phase. The final concentration of the capture reagent will normally be determined empirically to maximize the sensitivity of the assay over the range of interest. The conditions for incubation of sample and immobilized capture reagent are selected to maximize sensitivity of the assay and to minimize dissociation. Preferably, the incubation is accomplished at fairly constant temperatures, ranging from about 0° C. to about 40° C., preferably from about 20 to 37° C. The time for incubation depends primarily on the temperature, being generally no greater than about 10 hours to avoid an insensitive assay. Preferably, the incubation time is from about 0.5 to 3 hours, and more preferably 1.5-3 hours to maximize binding.

At this stage, the pH of the incubation mixture will ordinarily be in the range of about 4-9.5, preferably in the range of about 6-9, more preferably about 7-8, and most preferably the pH of the assay (ELISA) diluent is pH 7.4. The pH of the incubation buffer is chosen to maintain a significant level of specific binding. Various buffers may be employed allowing for the specific binding of an antibody to an epitope and generally include aqueous buffer systems or aqueous solutions at physiologic pH and ionic strength. Such buffers are, by way of non-limiting example, carbonate buffer, phosphate buffered saline, sodium phosphate buffer systems, Tris/HCl buffer, glycine buffer or acetate buffer. The pH of the buffer should range between 5 and 10. Salt concentrations are defined between 0 and 250 mmol/l using sodium chloride or an equivalent salt. Buffers may be supplemented with high salt concentrations up to 1 M to avoid unwanted interactions. The particular buffer employed is not critical to the invention, but in individual assays one buffer may be preferred over another.

In a further step, which is optional, the biological sample is separated (preferably by washing) from the immobilized capture reagent to remove uncaptured molecules. The solution used for washing is generally a buffer ("washing buffer") with a pH determined using the considerations and buffers described above for the incubation step, with a preferable pH range of about 6-9. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step.

In a next step, the immobilized capture reagent is contacted with detectable antibodies, preferably at a temperature of about 20-40° C., more preferably about 20-37° C., with the exact temperature and time for contacting the two being dependent primarily on the detection means employed. For example, when streptavidin-peroxidase and 3,3',5,5'-tetramethyl benzidine are used as the means for detection, e.g. in one embodiment, the contacting is carried out (e.g. about 1 hour or more) to amplify the signal to the maximum.

This antibody is directly or indirectly detectable. The detectable antibody may be a polyclonal or monoclonal antibody. Also the detectable antibody can be directly detectable, and in one embodiment has a colorimetric label, and in another embodiment has a flurometric label. More preferably, the detectable antibody is biotinylated and the detection means is avidin or streptavidin-peroxidase and 3,3',5,5'-tetramethyl benzidine. The readout of the detection means can be fluorimetric or colorimetric.

In a last step of the method, the level of antibody that is now bound to the capture reagent is measured using a detection means for the detectable antibody.

In a specific embodiment, the peptides as disclosed herein are deposited onto a carrier or solid phase and exposed to blood, serum, plasma or other antibody-containing body fluid such as mucosal secretions or smears. Consequently, so prepared compositions can be employed to identify and/or characterize an antigenic response of a subject against the specific peptides, and optionally assess the kind of response, for example identification of acute, recent primo, late, persistent or chronic infection, as well as efficacy of therapy, etc.

Direct coating via passive adsorption to the polystyrene surface of microplates in alkaline conditions is less efficient for peptide antigens compared to full-length proteins. Nevertheless, several technical solutions, like synthesis of peptide-dextran conjugates (Bocher et al. 1997), the use of a streptavidin-biotinylated peptide system (Ivanov et al. 1992), peptides bound to plastic of polyethylene pins or the use of a capture antibody (sandwich ELISA), have been developed to resolve these coating difficulties. As already mentioned, diagnostic assays contemplated herein may be based on numerous well known manners of detection, including ELISA (plate-based or solid phase; sandwich or non-sandwich), pinELISA, competitive ELISA, anti-idiotypic antibodies, direct fluorescent antibody test (DFA) etc., wherein all known colorimetric and photometric (e.g., fluorescence, luminescence, etc.) or radiometric reactions are deemed suitable for use.

In a further embodiment, the present invention provides a composition, kit or diagnostic kit comprising one or both of the peptides disclosed herein. Preferably, the kit comprises instructions on how to use the kit. In preferred embodiment said test kit is an ELISA.

Typically, the kit will comprise one or both of the peptides as disclosed herein, optionally in combination with other peptides or proteins, in suitable container(s), optionally bound to a solid support, such as for example a microtiter plate, a membrane, beads, dip sticks or the like. Alternatively, the support can be provided as a separate element of the kit.

Optionally, the kit according to the present invention further includes beside the peptide(s) disclosed herein a detection agent for the antibodies which may be an antibody, antibody fragment etc. If required, the kit further comprises substrate and further means for allowing reaction with an enzyme used as label for the detecting agent, which may be an antibody. The detection agent of the kit can include a detectable label that is associated with or linked to the given detecting agent, in particular, the detecting antibody. Detectable labels that are associated with or attached to a secondary binding ligand are also contemplated. Detectable labels include dyes, illuminescent or fluorescent molecules, biotin, radiolabels or enzymes. Typical examples for suitable labels include commonly known fluorescent molecules, like rhodamine, fluorescein, green fluorescent protein or luciferase, or alkaline phosphatase and horseradish peroxidase as examples for suitable enzymes.

Optionally, the kit further comprises positive and negative controls for verifying the results obtained when using the kit. The components of the kit can be packaged either in aqueous medium or lyophilised form and, in addition, the kit may comprise one or more containers allowing to conduct the detection. In addition, the test kit comprises instructions for use of the kit.

In a further embodiment, the present invention relates to the use of the peptide(s) or kit as disclosed herein in a method for diagnosing or detection of *C. suis* infection. Typically, the use is in vitro. The peptides can be used alone or in combination, and the combination can be a simultaneous, separate or sequential use in a method as described herein.

The invention also relates to a method for preparing the peptide(s) as disclosed herein. The peptide of the invention can be made using standard synthetic chemistry techniques, such as by use of an automated synthesizer. In the alternative, the peptide can be made from a longer polypeptide, which polypeptide typically comprises the sequence of the peptide. The peptide may be derived from the polypeptide by for example hydrolysing the polypeptide, such as using a protease; or by physically breaking the polypeptide. The peptide can also be made in a process comprising expression of a polynucleotide. The expressed polypeptide may be further processed to produce the peptide of the invention. Thus the peptide may be made in a process comprising cultivating a cell transformed or transfected with an expression vector under conditions to provide for expression of the peptide or a polypeptide from which the peptide can be made.

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

EXAMPLES

This study was funded by the Federal Public Service of Health, Safety of the Food Chain and Environment.

1. Material and Methods

Bacterial Strains

The following strains were used for production of experimental sera in 4-weeks-old piglets: *C. suis* strains S45, R19 and H7; *C. abortus* (S26/3); *C. psittaci* (98AV2129); *C. pecorum* (1710S). Bacteria were grown in cycloheximide treated McCoy cells according the standard methodology. Chlamydiae were released from infected monolayers by freezing and thawing prior to ultrasonication (Bransonic 12, BIOMEDevice, San Pablo, Calif., USA). Cell culture harvest was centrifuged for 10 min (1000×g, 4° C.) and Chlamydiae were subsequently concentrated by ultracentrifugation for 45 minutes (50,000×g, 4° C.). Bacteria were resuspended in 2 ml sucrose phosphate glutamate buffer (SPG, 218 mM sucrose, 38 mM $KH_2PO_4$, 7 mM $K_2HPO_4$, 5 mM L-glutamic acid) and stored at −80° C. until use.

Pig Sera

The used sera were derived from non-infected, naturally infected and experimentally infected/immunized pigs. For experimental infection of four-weeks-old SPF pigs, $10^6$ bacteria were used to infect piglets via aerosols, the oral and intravaginal route. Two pigs were infected with the C. suis reference strain S45. In addition, one pig was infected for each of the C. suis strains H7 and R19, the C. abortus S26/3 strain, and the C. psittaci 98AV2129 strain. Pigs were euthanized four weeks after infection.

For immunization of four-weeks-old SPF piglets, $10^6$ bacteria (of the C. abortus strain S26/3 or C. pecorum 1710S) were mixed with equal volumes of complete Freund's adjuvant (CFA; Sigma, Diegem, Belgium) and injected subcutaneously. Two weeks later, immunization was repeated to boost antibody production using incomplete Freund's adjuvant (Sigma, Diegem, Belgium). Pigs were euthanized three weeks after booster immunization and blood was collected. The used negative control sera were obtained from four-weeks-old SPF-piglets. Naturally infected pigs were sampled in a Belgian pig slaughterhouse. Blood and rectal swabs were collected from 83 animals, originating from 8 different farms. No information concerning the health status or antibiotic treatment of the sampled pigs was available. Swabs were stored in DNA/RNA stabilization buffer (Roche, Brussels, Belgium) at −80° C. for PCR analysis. DNA extraction was performed using the G-spin Total DNA Extraction Mini Kit (Goffin Molecular Biotechnologies, Beek, The Netherlands) according to the instructions of the manufacturer. The resulting DNA extract was analyzed using the C. suis specific real-time PCR (De Puysseleyr et al. 2014b), to confirm the presence of C. suis in the sampled pigs.

Additionally, a set of 10 sera originating from 4-weeks-old SPF-piglets were used as negative control sera.

All blood samples were incubated overnight at room temperature. Sera were collected, heat inactivated for 30 min at 56° C. and kaolin treated to reduce background reading (Novak et al. 1993). Four volumes of a kaolin suspension (25% (w/v) in PBS; pH 7.4) were added to one volume of serum and incubated at room temperature for 30 min. The samples were centrifuged (5500×g for 10 min) and the supernatant was stored at −20° C.

All sera were tested for the presence of anti-MOMP antibodies in a direct ELISA using C. trachomatis recombinant MOMP (CT rMOMP ELISA) as antigen (Schautteet et al. 2011). The test allows the detection of family-specific MOMP antibodies since the family specific epitope is located in the conserved region of MOMP (Stephens et al. 1998). The positive cut-off value was calculated as the mean of the OD-values of negative control pig sera plus twice the standard deviation.

Identification of the Pmp Sequences in the C. suis MD56 Genome

The putative C. suis Pmp sequences were extracted from the MD56 genome using Hidden Markov Models (HMMs). These HMMs were constructed using a seed set of sequences, consisting of manually curated pmps from 7 sequenced C. psittaci genomes (Cal10, 6BC, RD1, 01DC11, 02DC15, 08DC60 & C1998). Individual clustal alignments were independently run on each pmp family within the seed set and manually reviewed to conclude that no trimming was necessary. The hmmbuild tool of the HMMER package (Finn et al. 2011) was used to build a separate model for each pmp family. Results were reviewed and sequences split into sub-seeds to allow the generation of sub-family specific models. All HMMs were validated, again using the HMMER package (hmmsearch), against a larger set of C. psittaci and C. caviae sequences.

Selection of the Peptides

Pmp C

To determine the Pmp protein that is the best candidate to deliver C. suis specific antigens, the amino acid sequences of the nine Pmp proteins of *C. suis* MD56 were compared to the sequences of the reference strains A/Har-13 and L2/434/BU (*C. trachomatis*). The clustal omega program was used to construct multiple sequence alignments, using default parameters (Thompson et al. 1997). Nine regions (Table 1) were selected as templates for production of 152 synthetic peptides, which were produced by Pepscan Systems (Lelystad, The Netherlands). Peptides were eight amino acid residues in length, with an overlap of six residues. All peptides contained an N-terminal acetyl group and were C-terminal attached to polyethylene pins via incorporation of an extra cysteine at an amount of 100 μg per pin. The peptide coated pins were assembled on a polyethylene carrier in a '96-well format'. This enables the use of the pins for an ELISA assay in a 96-well microplate (referred to as 'pinELISA').

MOMP and Tarp

Identification of the *C. suis* specific regions using amino acid sequence alignments was combined with an epitope prediction of the identified sequences, for selection of a specific and immunogenic peptide. Alignments were constructed with the clustal omega program using default parameters (Thompson et al. 1997). The strains used to create the MOMP and Tarp alignments are listed in Table 2.

The B-cell epitope prediction of the identified *C. suis* specific regions was performed using tools provided by the Immune Epitope Database Analysis Resource (IEDB analysis resource). This provider offers a collection of six tools for the prediction of linear epitopes from protein sequences (Chou and Fasman Beta-Turn (Chou and Fasman 1978), Emini surface Accessibility (Emini et al. 1985), Karplus and Schulz Flexibility (Karplus and Schulz 1985), Kolaskar and Tongaonkar Antigenicity (Kolaskar and Tongaonkar 1990), Parker Hydrophilicity (Parker et al. 1986) and Bepipred Linear Epitope prediction (Larsen et al. 2006)).

Pin ELISA

Experimental Sera

Pins were blocked with blocking buffer (0.01M PBS [7.5 mM $Na_2HPO4$, 145 mM NaCl, 3.25 mM $NaH_2PO_4.2H_2O$; pH=7.2] supplemented with 0.1% Tween 20 and 5% BSA) for 3 hours, at room temperature (RT) and 100 rpm. Subsequently, pins were washed three times (washing buffer [0.01M PBS, 0.1% Tween 20], 10 min, 100 rpm). Sera were diluted in dilution buffer (0.01M PBS, 3% BSA, 0.1% Tween 20) and incubated overnight at 4° C. and 100 rpm. After another washing step, pins were incubated in a 1000-fold dilution of polyclonal HRP conjugated anti-swine IgG (H+L) antibody (Bethyl Laboratories, Montgomery, USA) for 1 hour at room temperature and 100 rpm. After a final washing step, the optical density (OD) at 405 nm was measured upon addition of hydrogen peroxide and ABTS substrate (KPL, Gaithersburg, Md., USA). Stripping of the bound antibodies after measurement enabled re-use of the pin peptides. Therefore, pins were sonicated (70° C., 40 kHz) for 1 hour in disrupt buffer solution (0.1M $Na_2HPO_4.2H_2O$, 35 mM SDS, 0.1% 2-mercapto-ethanol;

pH 7.2) followed by 30 min sonication in ultra pure water. Pin peptides were stored at −20° C.

For use in the pin ELISA, experimental sera were diluted to the minimal concentration needed to exceed the positive cut-off value in the CT rMOMP ELISA. Thus, all experimental sera were used at approximately the same anti-chlamydial antibody concentration, to reduce false positive results due to background reading.

Interpretation of Data

All data obtained with experimental sera were corrected for background signal using the values of the negative control serum. In order to find a *C. suis* specific and immunogenic antigen, peptides were selected with high OD-values for the anti-*C. suis* experimental sera and low OD-values for sera of animals infected/immunized with *C. abortus*, *C. psittaci* or *C. pecorum*.

Field Sera

The pin ELISA protocol was slightly altered to test the set of 'field sera', obtained by sampling SPF-piglets and finishing pigs (slaughterhouse). The blocking step was extended to an overnight incubation, and the sera were incubated for 1 hour at 37° C. instead of at 4° C. overnight. All field sera were tested in two dilutions: 1/100 and 1/500. The positive cut-off value was calculated as the mean of the OD values of negative control pigs sera plus twice the standard deviation and appeared to be 0.5.

2. Results

In Silico Selection of *C. suis* Specific Peptides

Pmps

The nine Pmp sequences of *C. suis* MD56 were compared to those of the *C. trachomatis* A/HAR-13 and L2/434/Bu strains to search for *C. suis* specific sequences. The overall sequence homology varied between 70 and 80%, except for PmpC, with a similarity of 58%. The lower sequence homology was partly due to the presence of *C. suis* specific inserts. Moreover, a PmpC coding gene was absent in the *C. abortus*, *C. psittaci* and *C. pecorum* reference genomes. Therefore, the PmpC was considered as the best Pmp candidate for selection of a specific antigen. The amino acid sequence alignments were used to search for the *C. suis* sequences with the highest divergence compared to *C. trachomatis*. Nine '*C. suis* specific regions' were ordered as overlapping pin peptides (eight amino acids in length with a six amino acid overlap) for further in vitro specificity testing (Table 1). The PmpC derived peptide is valuable for serodiagnosis in pigs as well as in *C. trachomatis* negative humans.

TABLE 1

Amino acid sequence and location of the nine selected '*C. suis* specific' regions. The PmpC protein of the MD56 strain contains 2141 amino acids.

| Amino acid Sequence | SEQ ID NO | Position in protein sequence |
| --- | --- | --- |
| SFSNISEEIQEPSSTPEQEENEETDEDSSLDSRNTEETPPSPSSETQEDD | 3 | 67-117 |
| QPQNNAIALRSFLYSLQTET | 4 | 147-167 |
| GAILGESTVTITGVDTLTFSKNAVKVTFVDKSETQNPSGGSGTGDSSDSSEAEGSSGSSND SANNSSGGDSNGVSAAAQAAAFSRFLSASTSTDPQPGEAENTDSTLNVKLGCGGGIYSK | 5 | 267-387 |
| PTDQEQGSQGTEQDSQEGSPGSTGSQESATNSASSQQSSIASARLTQLSL | 6 | 447-497 |
| GGGSSSPTSPQSPTTEVIKPVVGRGGAVYT | 7 | 587-617 |
| GNGQDQEQPGAEGGASEEDSNADSGQEVTG | 8 | 905-935 |
| VRSSSEDRAQEAGSDSTPSS | 9 | 995-1015 |
| EGDSESAEAS | 10 | 1115-1125 |
| AIGLVAGAIPADNNSVTATVSDSGTPSTTP | 11 | 1278-1308 |

MOMP

Similarly to the approach used for the PmpC, amino acid sequences were searched for *C. suis* specific regions, using alignments. The pairwise MOMP sequence similarity among the considered *C. suis* strains (Table 2) varied from 76% to 100%. As expected, *C. suis* is among all species mostly related to *C. trachomatis*, with observed homology percentages ranging from 64 to 86%. The overall sequence similarity for the five considered chlamydial species varied from 59 to 85%.

The multiple sequence alignment allowed the selection of a 52 amino acid region (residue 247 to 299) that is conserved among the considered *C. suis* strains and contains a high concentration of *C. suis* specific amino acid residues. In silico epitope prediction enabled the identification of an eight residue MOMP peptide (GTKDASID; SEQ ID NO: 1) containing 3 *C. suis* specific amino acids (underlined), able to discriminate *C. suis* from the *Chlamydia* species occurring in pigs. However, it was unfeasible to select a MOMP peptide antigen to distinguish *C. trachomatis* from all available *C. suis* sequences. Therefore, the MOMP peptide is only valuable for serodiagnosis in pigs. As well as the PmpC peptides, this MOMP peptide was purchased from pepscan (Lelystad, The Netherlands) in a pin ELISA format for further in vitro specificity testing.

TABLE 2

Overview of the chlamydial strains used to construct the amino acid sequence alignment to identify *C. suis* specific regions in the MOMP and Tarp protein.

| Species | Strain | Source |
| --- | --- | --- |
| MOMP | | |
| *C. suis* | H7, R16, R1, R33, H5, R19, S45, R24, | unpublished data |

TABLE 2-continued

Overview of the chlamydial strains used to construct the amino acid sequence alignment to identify C. suis specific regions in the MOMP and Tarp protein.

| Species | Strain | Source |
| --- | --- | --- |
| | 130 Rogers, R27, R22, R28 | |
| C. psittaci | 6BC | Genbank: Q46203.1 |
| C. pecorum | E58 | GenBank: ACH42158.1 |
| C. abortus | S26/3 | Genbank: YP_219480.1 |
| C. trachomatis | A/HAR-13 and 434/Bu | Genbank: AAX50959.1 and YP_007851996.1 |
| Tarp | | |
| C. suis | S45 | unpublished data |
| C. psittaci | 6BC | Genbank: WP_006342845.1 |
| C. pecorum | MC Marsbar | Genbank: AEF01186 |
| C. abortus | S26/3 | Genbank: WP_011096873.1 |
| C. trachomatis | A/HAR-13 and 434/Bu | Genbank: AAX50730.1 and Q6GX35.1 |

Tarp

Alignment of all available 158 C. trachomatis Tarp sequences shows a high sequence conservation, with pairwise sequence identities ranging from 91 to 100%. When comparing the C. suis S45 Tarp and C. trachomatis, on average 60% of the sequence is identical. The C. pecorum, C. psittaci and C. abortus Tarp sequence showed on average 33% sequence similarity to C. suis and C. trachomatis. The results of the protein sequence alignments, combined with epitope prediction, enabled the selection of the eight amino acid peptide with sequence 'GSSTPTAS' (SEQ ID NO: 12; amino acid residues 417 to 424 of the 842 residue protein).

In Vitro Selection of a PmpC Peptide

Optimization of Experimental Sera Dilution

The optimal dilution of the experimental sera for use in the pin ELISA, was determined by analysis of a two-fold dilution series in the CT rMOMP ELISA. The obtained optimal dilutions ranged from 1/3.5 to 1/896. More detailed results are represented in Table 3.

PmpC Peptide ELISA with Experimental Sera

The 152 PmpC peptides were screened for sensitivity and specificity for C. suis with the experimental sera. One peptide, with sequence SQQSSIAS (SEQ ID NO: 2), was selected based on maximal OD-values for C. suis antisera and minimal OD-values for C. abortus, C. psittaci and C. pecorum antisera.

TABLE 3

The optimal dilution of the experimental sera based on the results of the C. trachomatis rMOMP ELISA.

| Species | Strain | Titer |
| --- | --- | --- |
| C. suis[#] | S45_1 | 1/224 |
| | S45_2 | 1/112 |
| | H7 | 1/3.5 |
| | R19 | 1/7 |
| C. abortus[#] | S26/3_1 | 1/100 |
| C. abortus[*] | S26/3_2 | 1/896 |
| C. pecorum[*] | 1710S | 1/448 |
| C. psittaci[#] | 98AV2129 | 1/857 |

[*]sera obtained after immunization pigs;
[#]sera obtained after infection

Specificity Testing of MOMP and Tarp Peptides with Experimental Sera

Both peptides showed no cross reaction to the C. abortus, C. pecorum and C. psittaci antisera. Moreover, all C. suis antisera clearly reacted to the MOMP with OD-values exceeding the cut-off (0.5). However, for the Tarp peptide, the OD values of the C. suis S45_1 and R19 antisera did not reach the cut-off. Therefore, the Tarp peptide was no longer considered as an immunogenic antigen candidate and eliminated for further experiments.

Validation of the MOMP and PmpC Peptide Antigens

Molecular Characterization of Field Sera

The field sera, sampled in the slaughterhouse, were molecularly characterized, using two tests. The presence of C. suis bacteria in the sampled pigs was detected by examination of rectal swabs using the C. suis specific real-time PCR. Bacterial DNA was detected in 69 of 83 swabs. Furthermore, to detect anti-chlamydial antibodies, all sera were analyzed at a dilution of 1/100 using the CT rMOMP ELISA. Sixty-eight of 83 serum samples were positive. According to these results, the set of field samples originating from the slaughterhouse was divided in three groups: group A consisted of 64 sera originating from pigs that were positive in both real-time PCR and CT rMOMP ELISA, group B contained 9 sera and was subdivided in groups B1 and B2. The four sera of group B1 were sampled from PCR negative pigs and showed a clear response in the CT rMOMP ELISA. The five sera of group B2, sampled from PCR positive pigs, showed no response in the CT rMOMP ELISA. Group C comprises 10 sera negative in both tests.

Pin ELISA

The sera of group A, B and C were used to validate the performance of the selected peptides for use in detection of anti C. suis antibodies. An additional group (D) that contained sera of 10 SPF-animals, served as an extra negative control group. All field samples were tested at dilutions 1/100 and 1/500. However, the majority of the OD-values of the 100-fold dilutions reached the upper detection limit of the used technology, possibly partly due to background reading. Therefore, field samples were tested in a 500-fold dilution in subsequent experiments. The cut-off value was calculated at 0.5.

All sera of the negative control groups C and D were negative in the MOMP and PmpC peptide ELISAs. In 50 of 64 sera of the positive control group A, antibodies for both the PmpC and MOMP peptide were demonstrated. Twelve sera contained anti-PmpC peptide antibodies, but no anti-MOMP peptide antibodies. The two remaining sera showed no response for both candidate antigens. All sera of group B1 showed a clear response to the MOMP and PmpC peptide. In fact, this points at a prior infection since antibodies were present, but no bacteria could be demonstrated. For three (of five) sera of group B2, only anti-PmpC antibodies were demonstrated. The remaining two (of five) sera showed no response to both candidate peptides. This observation could be attributed to false positive results of the CT rMOMP ELISA. After all, cross-reaction with other pathogens is common when using full length proteins as antigens (Schautteet and Vanrompay 2011). Since the CT rMOMP ELISA is a family-specific assay, also antibodies produced in response to infections with other chlamydial species, are detected. In fact, mixed infections of chlamydial species regularly occur in pigs (Szeredi et al. 1996; Hoelzle et al. 2000).

Table 4 summarizes the obtained results of the field sera.

TABLE 4

Results of the *C. suis* real-time PCR, CT rMOMP ELISA and *C. suis* POMP C and MOMP peptide ELISA on 83 field sera.

| Group | Number of sera | Positive in *C. suis* real-time PCR | Positive in CT rMOMP ELISA | Positive in MOMP peptide ELISA | Positive in *C. suis* PmpC peptide ELISA |
|---|---|---|---|---|---|
| A | 64 | 64 | 64 | 50 [0.77; 0.33] | 62 [0.96; 0.34] |
| B1 | 4 | 0 | 4 | 4 [0.67; 0.08] | 4 [1.16; 0.33] |
| B2 | 5 | 5 | 0 | 0 | 3 [0.67; 0.15] |
| C | 10 | 0 | 0 | 0 | 0 |
| D | 10 | NP | 0 | 0 | 0 |

NP: not performed; The values of the average OD and associated standard deviations are respectively represented between brackets.

CONCLUSION

Analysis of the experimental sera and molecularly characterized field sera demonstrated the suitability of the MOMP and PmpC peptide antigens for use in serodiagnosis of *C. suis* in swine. Moreover, the PmpC peptide appeared more sensitive compared to the MOMP fragment.

REFERENCES

Andersen, A. A. and D. G. Rogers (1998). Resistance to tetracycline and sulfadiazine in swine *C. trachomatis* isolates. Ninth International Symposium on Human *Chlamydial Infection, San Francisco, Calif*.

Bocher, M., T. Boldicke, et al. (1997). "Synthesis of mono- and bifunctional peptide dextran conjugates for the immobilization of peptide antigens on ELISA plates: properties and application." Journal of Immunological Methods 208 (2): 191-202.

Borel, N., N. Regenscheit, et al. (2012). "Selection for tetracycline-resistant *Chlamydia suis* in treated pigs." Vet Microbiol 156(1-2): 143-146.

Brade, L., Rozalski, A., Kosma, P., Brade, H. (2000). A monoclonal antibody recognizing the 3-deoxy-D-manno-oct-2-ulosonic acid (Kdo) trisaccharide alphaKdo(2→4) alphaKdo(2→4)alphaKdo of *Chlamydophila psittaci* 6BC lipopolysaccharide." Journal of Endotoxin Research 6(5): 36368.

Cevenini, R., M. Donati, et al. (1991). "Partial Characterization of an 89-Kda Highly Immunoreactive Protein from *Chlamydia-Psittaci* a/22 Causing Ovine Abortion." Fems Microbiology Letters 81(1): 111-116.

Chou, P. Y. and G. D. Fasman (1978). "Prediction of the secondary structure of proteins from their amino acid sequence." Advances in enzymology and related areas of molecular biology 47: 45-148.

De Puysseleyr, K., L. De Puysseleyr, et al. (2014a). "Evaluation of the presence and zoonotic transmission of *Chlamydia suis* in a pig slaughterhouse." Bmc Infectious Diseases 14: 560.

De Puysseleyr, K., L. De Puysseleyr, et al. (2014b). "Development and Validation of a Real-Time PCR for *Chlamydia suis* Diagnosis in Swine and Humans." PloS one 9(5): e96704.

Dean, D., J. Rothschild, et al. (2013). "Zoonotic Chlamydiaceae Species Associated with Trachorna, Nepal." Emerging Infectious Diseases 19(12): 1948-1955.

Di Francesco, A., R. Baldelli, et al. (2006). "Seroprevalence to chlamydiae in pigs in Italy." Veterinary Record 159 (25): 849-850.

Di Francesco, A., M. Donati, et al. (2011). "Seroepidemiologic Survey for *Chlamydia suis* in Wild Boar (*Sus scrofa*) Populations in Italy." J of Wildlife Dis 47(3): 709-712.

Donati, M., A. Di Francesco, et al. (2009). "In vitro detection of neutralising antibodies to *Chlamydia suis* in pig sera." Veterinary Record 164(6): 173-174.

Eggemann, G., M. Wendt, et al. (2000). "Prevalence of *Chlamydia* infections in breeding sows and their importance in reproductive failure." DTW. Deutsche tierarztliche Wochenschrift 107(1): 3-10.

Emini, E. A., J. V. Hughes, et al. (1985). "Induction of Hepatitis-a Virus-Neutralizing Antibody by a Virus-Specific Synthetic Peptide." Journal of Virology 55(3): 836-839.

Finn, R. D., J. Clements, et al. (2011). "HMMER web server: interactive sequence similarity searching." Nucleic acids research 39(Web Server issue): W29-37.

Forsbach-Birk, V., C. Foddis, et al. (2013). "Profiling Antibody Responses to Infections by *Chlamydia abortus* Enables Identification of Potential Virulence Factors and Candidates for Serodiagnosis." PloS one 8(11).

Grimwood, J. and R. S. Stephens (1999). "Computational analysis of the polymorphic membrane protein superfamily of *Chlamydia trachomatis* and *Chlamydia pneumoniae*." Microbial & comparative genomics 4(3): 187-201.

Hoelzle, L. E., K. Hoelzle, et al. (2004). "Recombinant major outer membrane protein (MOMP) of *Chlamydophila abortus, Chlamydophila pecorum*, and *Chlamydia suis* as antigens to distinguish chlamydial species-specific antibodies in animal sera." Veterinary Microbiology 103 (1-2): 85-90.

Hoelzle, L. E., G. Steinhausen, et al. (2000). "PCR-based detection of chlamydial infection in swine and subsequent PCR-coupled genotyping of chlamydial omp1-gene amplicons by DNA-hybridization, RFLP-analysis, and nucleotide sequence analysis." Epidemiology and Infection 125(2): 427-439.

Ivanov, V. S., Z. K. Suvorova, et al. (1992). "Effective Method for Synthetic Peptide Immobilization That Increases the Sensitivity and Specificity of Elisa Procedures." Journal of Immunological Methods 153(1-2): 229-233.

Karplus, P. A. and G. E. Schulz (1985). "Prediction of Chain Flexibility in Proteins—a Tool for the Selection of Peptide Antigens." Naturwissenschaften 72(4): 212-213.

Kolaskar, A. S. and P. C. Tongaonkar (1990). "A Semiempirical Method for Prediction of Antigenic Determinants on Protein Antigens." Febs Letters 276(1-2): 172-174.

Larsen, J. E., O. Lund, et al. (2006). "Improved method for predicting linear B-cell epitopes." Immunome research 2: 2.

Lis, P., A. Kumala, et al. (2014). "Novel locked nucleic acid (LNA)-based probe for the rapid identification of *Chlamydia suis* using real-time PCR." Bmc Veterinary Research 10.

Longbottom, D. and L. J. Coulter (2003). "Animal chlamydioses and zoonotic implications." Journal of Comparative Pathology 128(4): 217-244.

Longbottom, D., S. Fairley, et al. (2002). "Serological diagnosis of ovine enzootic abortion by enzyme-linked immunosorbent assay with a recombinant protein fragment of the polymorphic outer membrane protein POMP90 of *Chlamydophila abortus*." Journal of Clinical Microbiology 40(11): 4235-4243.

Longbottom, D., E. Psarrou, et al. (2001). "Diagnosis of ovine enzootic abortion using an indirect ELISA (rOMP91B iELISA) based on a recombinant protein fragment of the polymorphic outer membrane protein POMP91B of *Chlamydophila abortus*." Fems Microbiology Letters 195(2): 157-161.

Marques, P. X., P. Souda, et al. (2010). "Identification of immunologically relevant proteins of *Chlamydophila abortus* using sera from experimentally infected pregnant ewes." Clinical and vaccine immunology: CVI 17(8): 1274-1281.

Niessner, A., C. Kaun, et al. (2003). "Polymorphic membrane protein (PMP) 20 and PMP 21 of *Chlamydia pneumoniae* induce proinflammatory mediators in human endothelial cells in vitro by activation of the nuclear Factor-kappa B pathway." Journal of Infectious Diseases 188(1): 108-113.

Novak, M., Z. Moldoveanu, et al. (1993). "Murine Model for Evaluation of Protective Immunity to Influenza-Virus." Vaccine 11(1): 55-60.

Parker, J. M. R., D. Guo, et al. (1986). "New Hydrophilicity Scale Derived from High-Performance Liquid-Chromatography Peptide Retention Data—Correlation of Predicted Surface Residues with Antigenicity and X-Ray-Derived Accessible Sites." Biochemistry 25(19): 5425-5432.

Sachse, K., E. Vretou, et al. (2009). "Recent developments in the laboratory diagnosis of chlamydial infections." Veterinary Microbiology 135(1-2): 2-21.

Schautteet, K., D. S. Beeckman, et al. (2010). "Possible pathogenic interplay between *Chlamydia suis, Chlamydophila abortus* and PCV-2 on a pig production farm." The Veterinary record 166(11): 329-333.

Schautteet, K., E. De Clercq, et al. (2013). "Tetracycline-resistant *Chlamydia suis* in cases of reproductive failure on Belgian, Cypriote and Israeli pig production farms." Journal of medical microbiology 62: 331-334.

Schautteet, K., E. Stuyven, et al. (2011). "Protection of pigs against *Chlamydia trachomatis* challenge by administration of a MOMP-based DNA vaccine in the vaginal mucosa." Vaccine 29(7): 1399-1407.

Schautteet, K. and D. Vanrompay (2011). "Chlamydiaceae infections in pig." Veterinary research 42(1): 29.

Stephens, R. S., S. Kalman, et al. (1998). "Genome sequence of an obligate intracellular pathogen of humans: *Chlamydia trachomatis*." Science 282(5389): 754-759.

Suchland, R. J., K. M. Sandoz, et al. (2009). "Horizontal Transfer of Tetracycline Resistance among *Chlamydia* spp. In Vitro." Antimicrobial Agents and Chemotherapy 53(11): 4604-4611.

Szeredi, L., I. Schiller, et al. (1996). "Intestinal *Chlamydia* in finishing pigs." Veterinary pathology 33(4): 369-374.

Tan, C., R. C. Hsia, et al. (2009). "*Chlamydia trachomatis*-Infected Patients Display Variable Antibody Profiles against the Nine-Member Polymorphic Membrane Protein Family." Infection and Immunity 77(8): 3218-3226.

Thompson, J. D., T. J. Gibson, et al. (1997). "The CLUSTAL_X windows interface: flexible strategies for multiple sequence alignment aided by quality analysis tools." Nucleic Acids Research 25(24): 4876-4882.

Vanrompay, D., T. Geens, et al. (2004). "Immunoblotting, ELISA and culture evidence for Chlamydiaceae in sows on 258 Belgian farms." Veterinary Microbiology 99(1): 59-66.

Verminnen, K., M. Van Loock, et al. (2006). "Evaluation of a recombinant enzyme-linked immunosorbent assay for detecting *Chlamydophila psittaci* antibodies in turkey sera." Veterinary research 37(4): 623-632.

Wang, J., L. L. Chen, et al. (2009). "A chlamydial type III-secreted effector protein (Tarp) is predominantly recognized by antibodies from humans infected with *Chlamydia trachomatis* and induces protective immunity against upper genital tract pathologies in mice." Vaccine 27(22): 2967-2980.

Wang, J., Y. Q. Zhang, et al. (2010). "Immunodominant Regions of a *Chlamydia trachomatis* Type III Secretion Effector Protein, Tarp." Clinical and Vaccine Immunology 17(9): 1371-1376.

Wehrl, W., V. Brinkmann, et al. (2004). "From the inside out—processing of the *Chlamydial* autotransporter PmpD and its role in bacterial adhesion and activation of human host cells." Molecular Microbiology 51(2): 319-334.

Wittenbrink, M. M., X. T. Wen, et al. (1991). "Bacteriological Investigations into the Incidence of *Chlamydia-Psittaci* in Organs from Swine and in Aborted Porcine Fetuses." Journal of Veterinary Medicine Series B-Zentralblatt Fur Veterinarmedizin Reihe B-Infectious Diseases and Veterinary Public Health 38(6): 411-420.

Zahn, I., L. Szeredi, et al. (1995). "Immunohistological Determination of *Chlamydia psittaci/Chlamydia pecorum* and *C. trachomatis* in the Piglet Gut." Journal of Veterinary Medicine Series B-Zentralblatt Fur Veterinarmedizin Reihe B-Infectious Diseases and Veterinary Public Health 42(5): 266-276.

The invention claimed is:

1. An in vitro method for detecting the presence of *Chlamydia suis* antibodies in a subject, comprising:

providing a biological sample from the subject, and analyzing the sample for the presence of antibodies against the peptide of SEQ ID NO: 1 (GTKDASID), or a peptide of an amino acid sequence being at least 75% identical thereto;

and/or against a peptide of SEQ ID NO: 2 (SQQSSIAS), or a peptide of an amino acid sequence being at least 75% identical thereto.

2. The method according to claim 1, whereby the presence of antibodies against one or both peptides is indicative for a past, early or late *Chlamydia suis* infection in the subject.

3. The method according to claim 1, characterized in that the biological sample from the subject is a body fluid.

4. The method according to claim 1, characterized in that the detected antibodies are of the IgA, IgM and/or IgG type.

5. The method according to claim 1, characterized in that the subject is a mammal.

6. The method according to claim 1, characterized in that the presence of antibodies is detected by use of an immunoassay.

7. The method according to claim 6, wherein the immunoassay is an enzyme linked immunosorbent assay (ELISA).

8. A kit for use in the diagnosis of a *Chlamydia suis* infection, comprising an isolated peptide of 8 to 30 amino acids long comprising one or more peptides selected from the group consisting of the amino acid sequence of SEQ ID NO: 1 (GTKDASID), the amino acid sequence of SEQ ID NO: 2 (SQQSSIAS), a sequence at least 75% identical to SEQ ID NO: 1, and a sequence at least 75% identical to SEQ ID NO: 2, wherein said peptide(s) are immobilized on a solid support.

9. The kit according to claim 8, said kit further comprising a detection agent, wherein said detection agent binds to antibodies bound to said one or more peptides immobilized on said solid support.

10. A method for diagnosing a *Chlamydia suis* infection comprising providing a biological sample from the subject, and analyzing the sample for the presence of antibodies against one or more peptides selected from the group consisting of the amino acid sequence of SEQ ID NO: 1 (GTKDASID), the amino acid sequence of SEQ ID NO: 2 (SQQSSIAS), a sequence at least 75% identical to SEQ ID NO: 1, and a sequence at least 75% identical to SEQ ID NO: 2, wherein said peptide(s) are immobilized on a solid support, and whereby the presence of antibodies to one or more of said peptides is indicative of a *Chlamydia suis* infection.

11. A method for differentiating a vaccinated subject from a naturally infected subject, comprising providing a biological sample from a subject, and analyzing the biological sample for the presence of antibodies against the peptide of SEQ ID NO: 1 (GTKDASID), or a peptide of an amino acid sequence being at least 75% identical thereto; and/or against a peptide of SEQ ID NO: 2 (SQQSSIAS), or a peptide of an amino acid sequence being at least 75% identical thereto, wherein the vaccinated subject is a subject vaccinated with a vaccine against *Chlamydia suis* that does not comprise SEQ ID NO:1 and SEQ ID NO:2, wherein the naturally infected subject is a subject infected with *Chlamydia suis*, and the presence of the antibodies is indicative of a natural *Chlamydia suis* infection.

12. A method of preparing a peptide of 8 to 30 amino acids long comprising one or more peptides selected from the group consisting of the amino acid sequence of SEQ ID NO: 1 (GTKDASID), the amino acid sequence of SEQ ID NO: 2 (SQQSSIAS), a sequence at least 75% identical to SEQ ID NO: 1, and a sequence at least 75% identical to SEQ ID NO: 2, wherein the peptides are produced by synthetic chemistry, polypeptide hydrolysis or recombinant expression.

13. The method according to claim 6, wherein the immunoassay is an immunofluorescence (IF) assay, radioimmunoassay (RIA), enzyme immunoassay, enzyme labeled immunoblot assay, or a luminescence based immunoassay.

14. The method according to claim 3, wherein the biological sample is a mucosal secretion or blood.

15. The method according to claim 3, wherein the biological sample is serum.

* * * * *

SEQUENCE LISTING

```
<160> NUMBER OF SEQ ID NOS: 12

<210> SEQ ID NO 1
<211> LENGTH: 8
<212> TYPE: PRT
<213> ORGANISM: Chlamydia suis

<400> SEQUENCE: 1

Gly Thr Lys Asp Ala Ser Ile Asp
1               5

<210> SEQ ID NO 2
<211> LENGTH: 8
<212> TYPE: PRT
<213> ORGANISM: Chlamydia suis

<400> SEQUENCE: 2
```

Ser Gln Gln Ser Ser Ile Ala Ser
1               5

<210> SEQ ID NO 3
<211> LENGTH: 50
<212> TYPE: PRT
<213> ORGANISM: Chlamydia suis

<400> SEQUENCE: 3

Ser Phe Ser Asn Ile Ser Glu Glu Ile Gln Glu Pro Ser Ser Thr Pro
1               5                   10                  15

Glu Gln Glu Glu Asn Glu Glu Thr Asp Glu Asp Ser Ser Leu Asp Ser
            20                  25                  30

Arg Asn Thr Glu Glu Thr Pro Pro Ser Pro Ser Ser Glu Thr Gln Glu
        35                  40                  45

Asp Asp
    50

<210> SEQ ID NO 4
<211> LENGTH: 20
<212> TYPE: PRT
<213> ORGANISM: Chlamydia suis

<400> SEQUENCE: 4

Gln Pro Gln Asn Asn Ala Ile Ala Leu Arg Ser Phe Leu Tyr Ser Leu
1               5                   10                  15

Gln Thr Glu Thr
            20

<210> SEQ ID NO 5
<211> LENGTH: 120
<212> TYPE: PRT
<213> ORGANISM: Chlamydia suis

<400> SEQUENCE: 5

Gly Ala Ile Leu Gly Glu Ser Thr Val Thr Ile Thr Gly Val Asp Thr
1               5                   10                  15

Leu Thr Phe Ser Lys Asn Ala Val Lys Val Thr Phe Val Asp Lys Ser
            20                  25                  30

Glu Thr Gln Asn Pro Ser Gly Gly Ser Gly Thr Gly Asp Ser Ser Asp
        35                  40                  45

Ser Ser Glu Ala Glu Gly Ser Ser Gly Ser Ser Asn Asp Ser Ala Asn
    50                  55                  60

Asn Ser Ser Gly Gly Asp Ser Asn Gly Val Ser Ala Ala Ala Gln Ala
65                  70                  75                  80

Ala Ala Phe Ser Arg Phe Leu Ser Ala Ser Thr Ser Thr Asp Pro Gln
                85                  90                  95

Pro Gly Glu Ala Glu Asn Thr Asp Ser Thr Leu Asn Val Lys Leu Gly
            100                 105                 110

Cys Gly Gly Gly Ile Tyr Ser Lys
        115                 120

<210> SEQ ID NO 6
<211> LENGTH: 50
<212> TYPE: PRT
<213> ORGANISM: Chlamydia suis

<400> SEQUENCE: 6

Pro Thr Asp Gln Glu Gln Gly Ser Gln Gly Thr Glu Gln Asp Ser Gln
1               5                   10                  15

```
Glu Gly Ser Pro Gly Ser Thr Gly Ser Gln Glu Ser Ala Thr Asn Ser
            20                  25                  30

Ala Ser Ser Gln Gln Ser Ser Ile Ala Ser Ala Arg Leu Thr Gln Leu
        35                  40                  45

Ser Leu
    50

<210> SEQ ID NO 7
<211> LENGTH: 30
<212> TYPE: PRT
<213> ORGANISM: Chlamydia suis

<400> SEQUENCE: 7

Gly Gly Gly Ser Ser Pro Thr Ser Pro Gln Ser Pro Thr Thr Glu
1               5                   10                  15

Val Ile Lys Pro Val Val Gly Arg Gly Gly Ala Val Tyr Thr
            20                  25                  30

<210> SEQ ID NO 8
<211> LENGTH: 30
<212> TYPE: PRT
<213> ORGANISM: Chlamydia suis

<400> SEQUENCE: 8

Gly Asn Gly Gln Asp Gln Glu Gln Pro Gly Ala Glu Gly Gly Ala Ser
1               5                   10                  15

Glu Glu Asp Ser Asn Ala Asp Ser Gly Gln Glu Val Thr Gly
            20                  25                  30

<210> SEQ ID NO 9
<211> LENGTH: 20
<212> TYPE: PRT
<213> ORGANISM: Chlamydia suis

<400> SEQUENCE: 9

Val Arg Ser Ser Ser Glu Asp Arg Ala Gln Glu Ala Gly Ser Asp Ser
1               5                   10                  15

Thr Pro Ser Ser
            20

<210> SEQ ID NO 10
<211> LENGTH: 10
<212> TYPE: PRT
<213> ORGANISM: Chlamydia suis

<400> SEQUENCE: 10

Glu Gly Asp Ser Glu Ser Ala Glu Ala Ser
1               5                   10

<210> SEQ ID NO 11
<211> LENGTH: 30
<212> TYPE: PRT
<213> ORGANISM: Chlamydia suis

<400> SEQUENCE: 11

Ala Ile Gly Leu Val Ala Gly Ala Ile Pro Ala Asp Asn Asn Ser Val
1               5                   10                  15

Thr Ala Thr Val Ser Asp Ser Gly Thr Pro Ser Thr Thr Pro
            20                  25                  30

<210> SEQ ID NO 12
```

-continued

```
<211> LENGTH: 8
<212> TYPE: PRT
<213> ORGANISM: Chlamydia suis

<400> SEQUENCE: 12

Gly Ser Ser Thr Pro Thr Ala Ser
1               5
```